United States Patent [19]

Degeorge et al.

[11] Patent Number: 5,770,629

[45] Date of Patent: Jun. 23, 1998

[54] SLURRY HYDROCARBON SYNTHESIS WITH EXTERNAL PRODUCT FILTRATION

[75] Inventors: Charles W. Degeorge, Chester; Min Chang, Warren, both of N.J.

[73] Assignee: Exxon Research & Engineering Company, Florham Park, N.J.

[21] Appl. No.: 857,604

[22] Filed: May 16, 1997

[51] Int. Cl.$^6$ .................................................. C07C 27/00
[52] U.S. Cl. .............................. 518/700; 502/21; 502/22; 502/53
[58] Field of Search .............................. 518/700; 502/21, 502/22, 53

[56] References Cited

U.S. PATENT DOCUMENTS

| | | | |
|---|---|---|---|
| 5,260,239 | 11/1993 | Hsia | 502/30 |
| 5,382,748 | 1/1995 | Behrmann et al. | 585/899 |
| 5,599,849 | 2/1997 | Jager et al. | 518/700 |

Primary Examiner—Gary Geist
Assistant Examiner—Jafar Parsa
Attorney, Agent, or Firm—Jay Simon

[57] ABSTRACT

A slurry hydrocarbon synthesis process employs a slurry filtration vessel external of the slurry reactor. Slurry from the reactor is passed through one or more gas and solids disengaging zones, one or more of which may be present in the reactor and vessel, to reduce the gas and solids content of the slurry before it contacts the filter in the vessel. The filter separates the slurry hydrocarbon liquid from the gas and solids as a filtrate which is sent to upgrading. Valves in gas and fluid conduits enable the filtration vessel to be isolated from the reactor for maintenance, to replace filters and to aid in controlling slurry flow through the vessel. A hydrogen rich gas may be injected into the filtration vessel to prevent catalyst deactivation. Slurry is hydraulically circulated between the reactor and vessel due to density differences while the reactor is operating.

15 Claims, 1 Drawing Sheet

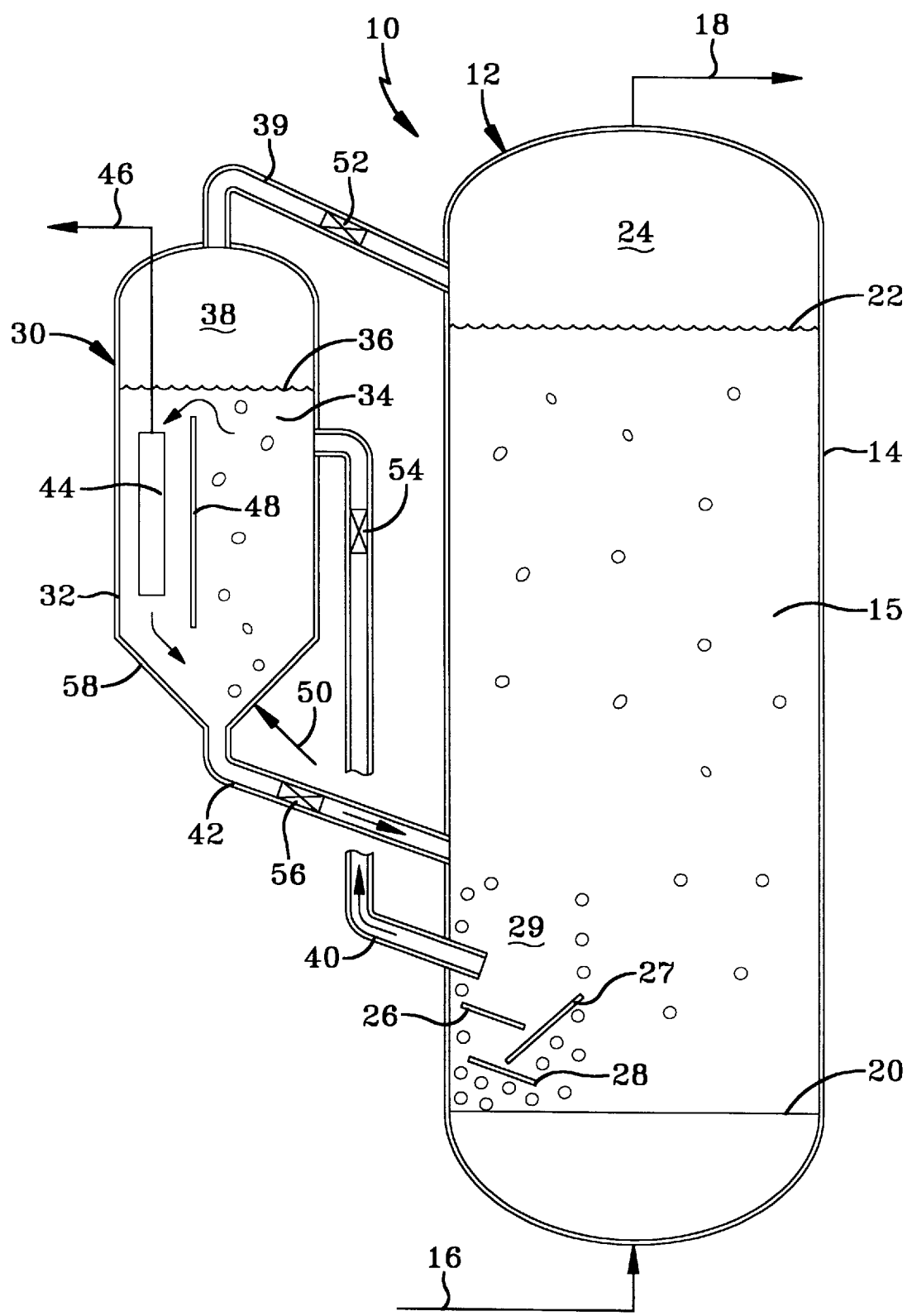

SLURRY HYDROCARBON SYNTHESIS WITH EXTERNAL PRODUCT FILTRATION

BACKGROUND OF THE DISCLOSURE

1. Field of the Invention

The invention relates to a slurry filtration process. More particularly, the invention relates to a process for filtering hydrocarbon liquid from a three phase hydrocarbon synthesis slurry comprising gas bubbles and particulate catalyst solids in a hydrocarbon liquid, wherein the filtration is conducted in a quiescent zone external of the slurry reactor and the gas and solids content of the slurry are reduced prior to filtration.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. The catalyst particles are typically kept dispersed and suspended in the liquid by the lifting action of the syngas bubbling up through the slurry and by hydraulic means. Mechanical means such as impellers and propellers and the like are not used, because they will quickly erode and also cause attrition of the catalyst particles. One or more vertical, gas disengaging downcomers may be used as hydraulic means to assist in maintaining more uniform catalyst dispersion, by providing a vertical catalyst circulation in the slurry, as is disclosed in U.S. Pat. No. 5,382,748. The slurry liquid comprises the liquid hydrocarbon products of the HCS reaction and must be separated from the catalyst particles and removed from the reactor for further processing and upgrading. This is typically accomplished by mechanical filtration in which the slurry is fed to one or more filters inside the slurry in the reactor, which permit the liquid to pass through, but not the catalyst particles. U.S. Pat. No. 5,527,473 and patent publications EP 0609079, WO 93/16796 and WO 94/16807 all relate to helically wound wedge wire filters and the like, while WO 93/16795 discloses vertical or helically wound fine metal threads or sintered metal. The filter or filtration surface is fully immersed in the reactive slurry inside the reactor. None of these processes reduce the solids and gas content of the slurry before it is filtered. Accordingly, there is a need for a filtration process in which at least some of the solid catalyst particles and gas bubbles are removed from the slurry prior to filtration.

SUMMARY OF THE INVENTION

The present invention relates to a filtration process for separating particulate solids from a liquid in a three phase hydrocarbon synthesis (HCS) slurry comprising gas bubbles and particulate solids in a hydrocarbon slurry liquid, in which the solids and gas content of the slurry are reduced prior to the separation, which takes place in a quiescent zone outside the slurry reactor. The process comprises withdrawing slurry from an HCS reactor and passing it into a combined filtration and gas and solids disengaging zone which contains one or more filters for separating and removing the hydrocarbon liquid from the slurry, and wherein at least a portion of the gas bubbles and catalyst particles are removed from the slurry before it contacts the filter. The filter is immersed in the slurry. The hydrocarbon slurry liquid passes into the filter from where it is removed as filtrate, with the catalyst solids remaining behind in the slurry. The filtrate is removed from the filtration zone and passed to storage or further processing and upgrading. Reducing the solids content of the slurry results in a greater liquid throughput through the filter and reduced fines in the filtrate. It also reduces the buildup of a catalyst particle filter cake. The combined filtration and gas and solids reducing zone is a separate vessel outside the reactor in fluid communication with the interior of the HCS slurry reactor and which can be isolated from the reactor by suitable isolation means, such as valves in the fluid conduits connecting the vessel to the reactor interior. This isolation feature enables filter removal and replacement without having to take the HCS reactor off-line. In one embodiment, slurry in the reactor is passed through a gas and solids disengaging zone in the reactor just upstream of the vessel inlet conduit, to disengage and remove a portion of the gas bubbles and solids from the slurry to form a gas and solids reduced slurry. This gas and solids disengaging zone may be located at any convenient height in the slurry in the reactor, with control of the slurry flow rate to the external vessel accomplished through hydrostatic head pressure differential and the use of control valves. After passing through the gas and solids disengaging zone in the reactor, the slurry is fed into the combined filtration and gas and solids reducing zone in the vessel external of the reactor, in which more gas bubbles and solids are disengaged from the slurry to form a gas and solids reduced slurry which contacts one or more filter means which separate the hydrocarbon slurry liquid from the solids and gas, as a filtrate. The filtrate may then be upgraded by fractionation and/or one or more conversion operations to more valuable products or sold neat. In this embodiment two gas and solids disengaging zones are employed, with the first within the slurry in the reactor and the second in the filtration zone external of the reactor. The external filtration is quiescent in that the slurry turbulence occurring in the reactor as a result of the uprising synthesis gas (syngas) does not occur in the filtration zone, as is explained in detail below. Any gas rising up in the quiescent zone is insufficient to keep the catalyst particles suspended in the slurry liquid. Therefore, catalyst particles disengage and fall down out of the slurry liquid. In another embodiment, slurry gas and solids disengagement takes place external of the reactor and not in the reactor. Still further, means such as a chordal baffle in the external filtration vessel separates the filtration zone from the rest of the slurry in the vessel. In this particular embodiment, gas and solids are removed from the slurry in the vessel before it contacts the filtration means. The baffle or equivalent means forms a quiescent filtration zone in which additional gas and solids are removed, before the slurry contacts the filter means. This quiescent zone is in fluid communication with the rest of the slurry in the vessel to provide circulation of the slurry in the vessel through the quiescent filtration zone and down and out of the vessel and back into the slurry reactor. Thus, two gas and solids disengaging zones are formed in the external filtration vessel by the baffle, one of which also comprises the actual filtration zone. Additional gas and solids may or may not occur upstream of the vessel, as in the embodiment in which such disengagement occurs within the slurry in the reactor. Therefore, the practice of the invention may employ multiple gas and solids disengagement in a plurality of such zones, at least one of which may be in the HCS reactor itself, with one or more in the external filtration vessel. Circulation of the slurry from the reactor into and through the external vessel and back into the reactor occurs by gravity due to hydrostatic heads and different slurry densities produced by the gas and solids reductions. In addition, control valves located in the slurry inlet and outlet lines of the filtration vessel can be used to further enhance control of the slurry flow rates. In a still further embodiment, the filtration vessel contains means for injecting a hydrogen rich gas into the slurry within, to avoid catalyst deactivation which can occur if all the hydrogen gas is removed or depleted from the slurry. While the invention is useful for removing liquid hydrocarbon product from a three phase slurry produced in a slurry hydrocarbon synthesis reaction, it is not intended to be limited to this particular embodiment.

The upper portion of the vessel comprises a gas collecting space or zone which is in communication with a gas space in the upper portion of the reactor, so that the pressure in the gas or vapor zone of the vessel is the same as that in the vapor or gas collecting zone in the top of the reactor. Filtrate withdrawal through the filter causes slurry in the reactor to pass through the gas and solids disengaging means and up into the upper portion of the slurry body in the vessel. Hydrostatic pressure differential produces slurry circulation between the reactor and filtration vessel without the need for pumps.

With specific regard to a slurry HCS process for forming hydrocarbons, at least a portion of which are liquid, the invention comprises the steps of:

(a) reacting a synthesis gas comprising a mixture of $H_2$ and CO in the presence of a solid, particulate hydrocarbon synthesis catalyst in a slurry body in a hydrocarbon synthesis reactor at reaction conditions effective to form hydrocarbons, at least a portion of which are liquid at said reaction conditions, wherein said slurry comprises said catalyst and gas bubbles in a hydrocarbon slurry liquid, and wherein slurry hydrocarbon liquid comprises said liquid hydrocarbons;

(b) passing a portion of said slurry from said slurry body through a gas and solids disengaging zone to form a gas and solids reduced slurry;

(c) passing said gas and solids reduced slurry into a quiescent filtration zone external of said reactor;

(d) contacting said gas and solids reduced slurry with filtration means in said quiescent filtration zone to separate a portion of said hydrocarbon liquid from said slurry as a filtrate to form a hydrocarbon reduced slurry, and (e) passing said hydrocarbon reduced slurry back into said slurry body in said reactor.

The hydrocarbon liquid filtrate is then sent to storage and/or upgrading to more valuable products. The filter means is immersed in the slurry in the filtration zone. The HCS reactor will typically be operating during filtration and the filtration may be continuous or intermittent. If the HCS reactor is on line and operating to produce hydrocarbons, filtering the hydrocarbon liquids and removing them from the reactor does not disturb or interfere with the HCS reaction in the reactor. One or more gas and solids disengaging zones may be in the HCS reactor, in the filtration zone, in-between both zones, or any combination thereof Baffle means, one or more gas and solids disengaging downcomers and the like, may be used to form a gas and solids disengaging zone in the slurry body in the reactor. In yet another embodiment, a hydrogen containing gas is fed into the external filtration zone or vessel to prevent catalyst deactivation.

BRIEF DESCRIPTION OF THE DRAWING

The FIGURE is a cross sectional schematic side view of a slurry type hydrocarbon synthesis unit useful in the process of the invention.

DETAILED DESCRIPTION

In a Fischer-Tropsch slurry HCS process, a syngas comprising a mixture of $H_2$ and CO is bubbled up into a reactive slurry in which it is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. The slurry liquid in the reactor comprises the hydrocarbon products of the hydrocarbon synthesis reaction which are liquid at the reaction conditions. A long standing problem has been the efficient separation and removal of the slurry hydrocarbon liquid product produced in the reactor from the relatively fine catalyst particles. The elevated temperature and pressure in the reactor and the waxy nature of the reaction hydrocarbon products make conventional particulate separation and filtration methods unsuitable for use in a slurry type hydrocarbon synthesis process. Thus, cyclone separation which has found such widespread use for separating catalyst particles from product vapors in cat cracking processes, is unsuitable for use with a waxy slurry, as are rotary and centrifuge filters While the temperature and pressure in the slurry can vary widely depending on the particular catalyst used and products desired, typical conditions effective to form hydrocarbons comprising mostly $C_{5+}$ paraffins, (e.g., $C_{5+}-C_{200}$) and preferably $C_{10+}$ paraffins, in a slurry HCS process employing a catalyst comprising a supported cobalt component include, for example, temperatures, pressures and hourly gas space velocities in the range of from about 320°–600° F., 80–600 psi and 100–40,000 V/hr/V, expressed as standard volumes of the gaseous CO and $H_2$ mixture (0° C., 1 atm) per hour per volume of catalyst, respectively. The slurry typically contains from about 10 wt. % to 70 wt. % catalyst solids, more typically from 30 wt. % to 60 wt. % and in some embodiments 40 wt. % to 55 wt. % is preferred. As mentioned above, the slurry liquid comprises hydrocarbon products which are liquid at the reaction conditions, along with minor amounts of other components. While catalyst particle sizes may broadly range from as small as 1 to as large as 200 microns, a typical conventional Fe or supported iron catalyst will have a mean particle size of about 22 microns, while a catalyst comprising a catalytic metal such as cobalt composited with or supported on titania will typically have a mean particle size of about 63 microns. However, such catalysts will also include fine particles as small as 1 micron and the constant agitation and mixing of the catalyst particles in the slurry results in particle size reduction through attrition. This also produces fines having a particle size of from about 1 to 10 microns. It is not possible to filter out such fine particles with the massive and bulky wound wire prior art filters. This results in some of the catalyst particles being withdrawn through these filters along with the hydrocarbon liquid and these particles must be removed before the hydrocarbon liquid product is sent to upgrading. Further, removing the prior art bulky filters from the reactor invariably means shutting down the reactor and draining the liquid out of it so that a clogged or damaged filter can be replaced or repaired. The drained liquid has to be sent to hot storage so that it does not solidify and then returned back into the reactor and heated up to enable continuation of the HCS reaction.

Referring now to the FIGURE which demonstrates the process and an apparatus of an embodiment of the invention, a slurry hydrocarbon synthesis unit 10 comprises a slurry reactor 12 having a hollow steel cylindrical shell 14 containing a three phase slurry 15 within, a syngas inlet 16 at the bottom and a gas outlet 18 at the top to remove unreacted syngas and gas products of the HCS reaction. The slurry comprises gas bubbles and catalyst particles dispersed in a hydrocarbon slurry liquid. The slurry liquid comprises hydrocarbon products of the HCS reaction which are liquid at the reaction conditions. The syngas is injected up into the slurry via suitable gas distribution means (not shown) arranged across the surface of an otherwise gas and liquid impermeable steel tray 20. The upward rising gas bubbles are briefly indicated by the small circles. A gas space 24 is above the top 22 of the slurry in the reactor for disengaging liquid and catalyst fines entrained in the uprising gas bubbles, which comprise a mixture of unreacted syngas and gas hydrocarbon synthesis products. The uprising bubbles of syngas keep the catalyst dispersed in the slurry. Catalyst dispersion may be assisted by means of vertical, gas disengaging downcomers (not shown) which set up a vertical slurry circulation as disclosed in U.S. Pat. No. 5,382,748. A filtration vessel 30 comprising a cylindrical steel outer shell 32 contains a slurry 34 within, the top 36 of which is lower than the level of the top of the slurry 22 in the reaction vessel. A gas space 38 above the slurry is in fluid communication with the gas space 24 in reactor 12 via gas line 39. The slurry 34 in the filtration vessel is in fluid communication with the slurry 15 in reactor 12 via slurry inlet and outlet conduits 40 and 42, respectively. Although the slurry entrance to conduit 40 is shown as located relatively low in the slurry body, it may be located at any convenient or desired vertical level in the slurry. Slurry flow from the slurry body 15 into the filtration vessel 30 is accomplished through hydrostatic head pressure differentials and the use of control valves or isolation valves 54 and 56. These valves enable the external filtration vessel to be isolated from the reactor for repair, maintenance and filter removal without disturbing the operation of the reactor and without the need for draining the reactor. They also assist in controlling the circulation or flow rate of the slurry from inside the reactor, to and through the external filtration zone and back into the reactor. At least one filter, briefly illustrated as a rectangular box 44, is immersed in slurry 34 for separating the slurry liquid from the particulate catalyst solids and withdrawing the liquid hydrocarbon filtrate from the filter and filtration vessel, via filtrate line 46. Since the top and bottom of both vessels are in fluid communication, the pressure in both vessels is about the same. However, since the overall gas concentration of the slurry in the filtration vessel or zone is substantially less than that of the slurry in the reactor, the liquid level is shown as below the level of the less dense slurry in the reactor. Maintaining pressure in filtrate withdrawal line 46 lower than that in the filtration zone or vessel 30 assures a steady flow of liquid from reactor 12 into vessel 30 without the need of pumps. Filter 44 may be a wound wedge wire filter of the prior art or a sintered metal filter having a porous outer surface defining a filtrate cavity within which is in liquid communication with filtrate withdrawal line 46. In a preferred embodiment, the filter or filters are removably secured in the slurry liquid by means such as a detachably attached plate (not shown) bolted over a flanged nozzle (not shown) at the top of the vessel from which they are suspended, as will be appreciated by those skilled in the art. In this embodiment, the filter is sized so as to be removable vertically upward from the filtration vessel through the nozzle for repair or replacement without having to drain the slurry from the filtration vessel. In a further embodiment (not shown) the bottom of the filter may terminate in a downwardly depending rod or other means slidably mounted in a sleeve attached to and depending upward from the bottom, to permit vertical, but not horizontal movement of the bottom of the filter unit and thereby accomodate thermal expansion and contraction. Baffles 26, 27 and 28 define a quiescent gas and solids disengaging zone 29 in the slurry reactor, upstream of the filter and filtration vessel. These baffles deflect the uprising gas bubbles away from the entrance of the slurry liquid inlet conduit 40. The quiescent zone 29 created in the slurry by the baffles, enables slurry in that zone to release gas bubbles and catalyst solids as it passes from the slurry body 15 in the HCS reactor into the inlet of conduit 40. This is due to the fact that the uprising gas bubbles are not being fully replaced and it is primarily the lifting action of the uprising gas bubbles which keeps the catalyst particles dispersed in the slurry liquid. The baffles also permit the disengaged slurry particles, which are heavier than the slurry liquid, to fall down into the slurry body below into which the uprising syngas bubbles are present, which lift and redisperse the catalyst particles up around the baffles and into the surrounding slurry body. At least a portion of the gas bubbles are disengaged from the slurry in the quiescent zone, due to the fact that slurry in that zone is not being contacted with the uprising syngas bubbles. Therefore, the disengaging, uprising gas bubbles in the quiescent zone are not fully replaced with uprising gas bubbles and this results in a gas and solids depleted slurry formed in the quiescent zone which rises up through conduit 40 and into the external filtration vessel 30 near to the top of the slurry in that vessel, as shown in this embodiment. If the entrance to conduit 40 is located proximate the top of the slurry body 15 in the reactor, a quiescent zone proximate the entrance may be formed by baffles. Alternatively, a gas disengaging downcomer similar to that disclosed in U.S. Pat. No. 5,382,748 may form the entrance to conduit 40 to feed a gas depleted slurry into the conduit. The slurry at the top of the slurry body 15 typically is leaner in solids than nearer to the bottom of the slurry. A gas and solids disengaging downcomer is preferable, if a downcomer is used, so that the slurry fed into the filtration zone is depleted in solids. The interior of the slurry filtration vessel 30 comprises another, relatively quiescent, gas and solids disengaging zone. Consequently, additional gas and catalyst solids are disengaged by the slurry passing through, from and back into the HCS reactor. The slurry flow through the external vessel is minimized to a low rate sufficient to remove the hydrocarbon liquids produced by the HCS reaction as needed to maintain system level control, plus a small additional quantity of liquid sufficient to suspend and return any solids which have entered the external vessel back into the main slurry body in the reactor.

In the prior art referred to above, the filter is fully immersed in the main slurry in the HCS reactor. As the prior art teaches, the uprising syngas bubbles serve to lift up the catalyst particles and keep them dispersed and suspended in the slurry. The '748 patent referred to immediately above teaches that gas disengaging downcomers fully immersed in the main slurry body can provide a downward flow which, when it exits the bottom of the downcomer near to the bottom of the slurry, it can provide a net upward flow of main body slurry sufficient to reduce vertical catalyst concentration maldistribution. The superficial gas velocity of the upward flowing gas bubbles in the main slurry body may range from about 5 to 70 cm/sec, as disclosed in EP 0609079A. Thus, considerable turbulence exists in the main slurry body, although the net slurry flow is near zero. This turbulence exhibits itself as surges flowing up, down, radially inward, radially outward, as swirls, etc. All this turbulence assists in maintaining a relatively uniform catalyst concentration throughout the main slurry body. In marked contrast, in a quiescent zone of the invention, any gas bubbles rising up are not sufficient to lift up the catalyst particles. The only occasion for injecting gas into the slurry in the filtration will be a relative trickle of hydrogen or a hydrogen containing gas in an amount sufficient to prevent catalyst deactivation and, if any CO is present in the slurry, to maintain the $H_2$ to CO mole ratio at least stoichiometric to prevent coking of the catalyst. Therefore, little or no turbulence is present in the quiescent and this permits further gas and solids disengagement so that the catalyst concentration and slurry velocity proximate the filter surface is very low (e.g., less than 30%), compared to that in the main slurry body in the reactor.

In the embodiment shown in the FIGURE, a chordal baffle 48 located in vessel 30 provides an additional quiescent zone proximate the filter 44, which substantially isolates the slurry on the filter side of the baffle from gas and turbulence in the main slurry body in the vessel that may occasionally somehow find its way into the external vessel. This additional quiescent zone permits further disengagement of catalyst particles and gas bubbles from the slurry in the vicinity of the filter. This causes the slurry on the filter side of the chordal baffle to be slightly more dense than that on the other side of the baffle. As a consequence, slurry from the main slurry body in the filtration vessel flows over the top of the baffle as indicated by the arrow, as the slightly heavier slurry on the filter side of the baffle has a slightly greater downward velocity. In a still further embodiment, hydrogen or a hydrogen containing gas is injected into the slurry in vessel 30 by means of gas line 50 and suitable gas injection means (not shown). This embodiment is optional and the hydrogen, if used, is injected into the bottom of the vessel if needed to prevent deactivation of the catalyst particles therein. It has been found that if all of the gas is removed from the slurry, the catalyst will deactivate and this deactivation may not be fully reversible. Consequently, if the catalyst particles are permitted to deactivate, depending on the degree of deactivation, the reactor may have to be taken off line, the slurry removed and the liquid separated from the catalyst, the catalyst processed to reactivate it, and the liquid and catalyst returned to the off-line reactor, which must then be heated and restarted to get it operating again. The hydrogen gas is injected into the vessel in a manner such that most of it is. bubbled up into the slurry in the non-filter side of the chordal baffle. If a chordal or other baffle is not employed to provide a separate filtration zone in the vessel, the hydrogen gas is injected into the slurry in a manner such that most of the gas bubbles are injected up into the slurry away from the vicinity of the filter to prevent other than minimal disturbance of the slurry adjacent the filter surface of the filter. Still further, in the context of the invention, the term "filter" is meant to include the one or more filters in the filtration vessel. Returning to the FIGURE, valves 52, 54 and 56 respectively shut of gas conduit 39, slurry inlet conduit 40 and slurry outlet conduit 42. These valves permit the vessel to be isolated from the HCS reactor to permit maintenance, repairs and filter replacement repair without having to shut down the HCS reactor or take it off-line.

In operation, the baffles at the entrance of slurry inlet of conduit 40 reduce gas and solids to form a gas and solids reduced slurry which rises up conduit 40 and into vessel 30. In vessel 30, more solids and gas are disengaged from the slurry, with the gas going up into gas collecting zone 38 from which it is removed and returned to the HCS reactor via gas conduit 39. A portion of this further gas and solids reduced slurry passes around the chordal baffle into the second quiescent zone, which is the filtration zone in which more gas and solids are disengaged from the slurry before it contacts the filter. This provides maximum liquid throughput into the interior of the filter, with minimal catalyst particle build up on the filter as filter cake. The additional quiescent zone, which is the filtration zone, also insures the passage of less fines (if present) into the interior of the filter, as more time for solids disengagement is provided. The gas reduced slurry passes out of the vessel and returns back into the HCS reactor via slurry exit conduit 42. The sloping bottom (e.g., cone shaped) of the vessel and the angle of the sloping transverse portion of the slurry exit conduit are greater than the angle of repose of the slurry solids, to prevent build-up of the solids in the vessel and conduit and concomitant plugging. Similarly, the angle of the sloping transverse portion of slurry inlet conduit 40 is also greater than the angle of repose of the solid particles. The denser slurry in the vessel flows back into the HCS reactor by gravity. The hydrostatic pressure exerted by the greater slurry height in the HCS reactor is sufficient to push the gas and solids reduced slurry up into the vessel 30 through the slurry inlet conduit 40. Maintaining pressure in the interior filtrate zone or chamber in the one or more filters 44 immersed in the slurry in vessel 30 sufficiently below the pressure in the HCS reactor and vessel (both of which are at the same pressure), provides a pressure differential driving force across the filter surfaces to force the slurry liquid through and into the interior filtrate zone of the one or more filters. The hydrocarbon liquid filtrate is removed via line 46 and sent to further processing and upgrading into more useful products. The disengaged gas released at the top of the vessel and transferred into the top of the reactor via conduit 39, is removed from the reactor via gas line 18 along with the unreacted syngas and gas products of the HCS reaction.. Disengaged solids fall to the bottom 58 of the vessel, down through the conduit 42 and back into the reactor. In this embodiment, the sloped wall 58 of the vessel is cone shaped and its angle is greater than the angle of internal friction of the catalyst particles, as is the slope of conduit 42, so that the catalyst particles do not build up in either the vessel or in the conduit. Finally, while the practice of the invention is not limited to any specific filter or filter design, in one embodiment it is preferred that the filter comprise a plurality of elongated, hollow, sintered metal filter elements in internal fluid communication with a filtrate conduit for removing the hydrocarbon liquid filtrate from the filter and out of the filtration vessel.

In an HCS process, liquid and gaseous hydrocarbon products are formed by contacting a syngas comprising a mixture of $H_2$ and CO, under shifting or non-shifting conditions and preferably under non-shifting conditions in which little or no water gas shift reaction occurs, particularly when the catalytic metal comprises Co, Ru or mixture thereof Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A slurry hydrocarbon synthesis process for forming hydrocarbons comprising:

(a) reacting a synthesis gas comprising a mixture of $H_2$ and CO in the presence of a solid, particulate hydrocarbon synthesis catalyst in a slurry body in a hydrocarbon synthesis reactor at reaction conditions effective to form hydrocarbons, at least a portion of which are liquid at said reaction conditions, wherein said slurry comprises said catalyst and gas bubbles in a hydrocarbon slurry liquid, and wherein said slurry hydrocarbon liquid comprises said liquid hydrocarbons;

(b) passing a portion of said slurry from said slurry body through a gas and solids disengaging zone to form a gas and solids reduced slurry;

(c) passing said gas and solids reduced slurry into a quiescent filtration zone external of said reactor;

(d) contacting said gas and solids reduced slurry with filtration means in said quiescent filtration zone to separate a portion of said hydrocarbon liquid from said slurry as a filtrate to form a hydrocarbon reduced slurry, and (e) passing said hydrocarbon reduced slurry back into said slurry body in said reactor.

2. A process according to claim 1 wherein slurry from said slurry body is passed through more than one gas and solids disengaging zone before it contacts said filter.

3. A process according to claim 2 wherein at least one gas and solids disengaging zone is present in said external filtration zone.

4. A process according to claim 3 wherein a gas and solids disengaging zone is present in said slurry body in said reactor.

5. A process according to claim 4 wherein said filtration zone and reactor each have a vapor space at the top thereof and wherein said vapor spaces are at the same pressure.

6. A process according to claim 5 wherein said filtration zone may be isolated from said reactor.

7. A process according to claim 6 wherein two gas and solids disengaging zones are present in said filtration zone.

8. A process according to claim 7 wherein said filtration means is removably secured in, and removable vertically upward from, said filtration vessel.

9. A process according to claim 8 wherein a hydrogen rich gas is injected into said slurry in said filtration zone.

10. A process according to claim 9 wherein said hydrogen rich gas is not sufficient to keep said particles suspended in said slurry in said filtration zone.

11. A process according to claim 1 wherein at least a portion of said filtrate is subjected to conversion.

12. A process according to claim 11 wherein the conversion process is non catalytic.

13. A process according to claim 11 wherein the conversion process is catalytic.

14. A process according to claim 13 wherein hydrogen is present in the catalytic conversion.

15. A process according to claim 14 wherein the catalytic conversion is hydroisomerization.

* * * * *